United States Patent [19]

Evans

[11] Patent Number: 4,953,556
[45] Date of Patent: Sep. 4, 1990

[54] METHOD AND APPARATUS FOR THE MEASUREMENT OF THORACIC FIELD POTENTIOMETRY

[76] Inventor: John M. Evans, Bell Cottage, Oaksmere, Appleton, Abingdon, Oxfordshire, OX13 5JS, United Kingdom

[21] Appl. No.: 162,256

[22] Filed: Feb. 29, 1988

[30] Foreign Application Priority Data

Dec. 13, 1984 [GB] United Kingdom ............... 8431500

[51] Int. Cl.⁵ .......................................... A61B 5/205
[52] U.S. Cl. .................................... 128/671; 128/693; 128/713; 128/734; 128/642
[58] Field of Search .............................. 128/670–671, 128/691–694, 713, 734, 642, 644

[56] References Cited

U.S. PATENT DOCUMENTS

| | | | |
|---|---|---|---|
| 4,198,963 | 4/1980 | Barkalow et al. | 128/642 X |
| 4,450,527 | 5/1984 | Sramek | 128/694 X |
| 4,836,214 | 6/1989 | Sramek | 128/693 |
| 4,852,580 | 8/1989 | Wood | 128/693 |

Primary Examiner—Angela D. Sykes
Attorney, Agent, or Firm—Cushman, Darby & Cushman

[57] ABSTRACT

Apparatus for measuring cardiac and/or pulmonary activity, comprising an electrical oscillator, a pair of electrodes for applying the oscillating electrical signal to the thorax of a patient, an oesophageal probe including an oesophageal electrode, a sensing electrode adapted to be positioned on the chest of the patient in the region of the apex of the heart, whereby measurement of voltage between the said first and second electrodes provides a measure of cardiac volumes, a third electrode adapted to be positioned on the chest of the patient at a position on the right side of the chest generally corresponding with that of the second electrode of the left side of the chest, whereby measurement of voltage between the said first and third electrodes provides a measure of volume of the right lung of the patient, a device for measuring the voltage induced between the first and second, and the first and third electrodes respectively, and for thereby providing first and second output signals respectively, indicative of cardiac and pulmonary activity respectively.

17 Claims, 6 Drawing Sheets

SIGNAL FROM ELECTRODES 8a AND 8b.

FIG. 12

SIGNAL FROM ELECTRODES 8b AND APICAL SURFACE ELECTRODE (e.g. 6)

FIG. 11

SIGNAL FROM ELECTRODES 8a AND APICAL SURFACE ELECTRODE (e.g. 6)

METHOD AND APPARATUS FOR THE MEASUREMENT OF THORACIC FIELD POTENTIOMETRY

BACKGROUND OF THE INVENTION

This invention relates to the measurement of heart and lung volume, using the technique of measuring thoracic generated field potentials. A number of techniques have been devised in recent years for the measurement of heart and lung volume of patients by the application to the thorax of the patient of an oscillating electrical current, and the measurement of the resulting voltages produced in the thorax across the organs of interest.

Examples of previous proposals include those by D.W. Hill and B.W. Watson (IEE. Medical Electronics monographs (1-6) published by Peter Peregrinus Limited, 1971), W.G. Kubicek, R.P. Patterson, and D.A. Witso (Annals of the New York Academy of Sciences, vol 170, article 2, pages 724-732, 1970), and B. Tedner, D. Linnarsson, and T. Ribbe (World Congress on Medical Physics and Biomedical Engineering 1982, Hamburg).

In these previously proposed methods of measurement, in general, potential differences are measured using electrodes applied to the body externally, either as point electrodes, or on either side of the chest, or as an array of strip electrodes applied longitudinally or circumferentially around the neck and lower thorax.

In a paper in Anesthesia (1983 Volume 38, pages 892-897), A.B. Baker and C. McLeod refer to the use of an oesophageal electrical probe for various measurements within the chest region, for example ECG, pacing, temperature, sound measurement, and pressure measurement.

In the paper by Baker and McLeod, reference is also made to the measurement of transthoracic impedance, using an external circumferential electrode system, with an internal oesophageal electrode system, or using a system with all internal electrodes.

Inherent in impedance measurement techniques is an assumption that all of the applied current flows between the voltage measuring electrodes. Given this assumption Ohm's Law can be applied to the known constant current and the measured potential difference to calculate the impedance of the tissues lying between the measurement electrodes. If an electric current is applied to the thorax and measurements of the potential difference between points within the thorax are made, then no reliable assumption can be made on the value of current flowing between these measuring electrodes. The generated field potential can be measured but no calculation of impedance of the tissues between the electrodes is possible. Changes in the generated field potential will arise from changes in the distribution of the field within individual organs within the thorax. Thus by positioning a pair of electrodes on either side of an individual organ, e.g. the heart, changes in the generated field potential will predominately reflect changes in the impedence of that organ; the changes in the impedance of the organ will in turn arise from changes in its volume and content.

We have now found that, by the careful placement of an external electrode on the chest, coupled with the use of an electrode in the oesophagus such as that suggested by Baker and McLeod, it is possible to localize accurately the volume responsible for voltage changes, and thus to measure cardiac volume, and by measuring the change of cardiac volume with time, cardiac stroke volume.

Accordingly, in a first aspect of the invention, there is provided a method of measuring cardiac activity, which method comprises generating an oscillating electrical signal, applying the oscillating electrical signal to the thorax of a patient, providing a second electrode on the chest of the patient in a position such that measurement of voltage between the said first and second electrodes provides a measure of cardiac volume, and measuring the voltage induced between the first and second electrodes and producing therefrom an output signal indicative of cardiac activity in the patient.

We have also discovered that by placement of a further electrode on the chest, it is possible to form separate assessments using a single piece of apparatus of heart stroke volume, and also lung tidal volume. This is achieved by so constructing the apparatus as to provide two measurements of generated potentials in selected locations, rather than one. In a further development, we have discovered that, by applying to a voltage measurement indicative of heart stroke volume, a correcting signal derived from the lung volume signal, it is possible to exclude from the heart stroke volume signal a substantial amount of "noise", due to fluctuating changes in trans-pulmonary voltage. Similarly, by applying a correcting signal derived from this heart volume signal to the lung volume signal, it is possible to improve the signal to noise ratio of the lung volume signal.

Accordingly, in a first aspect of the invention, there is provided apparatus for measuring heart volume and/or lung volume, which apparatus comprises means for generating an oscillating signal, means for applying the oscillating electrical signal to the thorax of a patient, an oesophageal probe including a first electrode, a second electrode adapted to be positioned on the chest of the patient in the region of the apex of the heart, whereby measurement of voltage between the said first and second electrodes provides a measure of heart volume, a third electrode adapted to be positioned on the chest of the patient at a position on the right side of the chest generally corresponding with that of the second electrode of the left side of the chest, whereby measurement of voltage between the said first and third electrodes provides a measure of volume of the right lung of the patient, and means for measuring the voltage induced between the first and second, and the first and third electrodes respectively, and for thereby providing first and second output signals respectively, indicative of heart volume and lung volume respectively.

The apparatus preferably includes means for varying either one of the output signals in dependence upon the other of the said output signals, for example by adding to the respective output signal a correcting signal, which may be simply the other signal, with an appropriate amplitude modification, or phase shift. Means may be provided for varying automatically the proportion of, for example, the lung signal which is used as a correcting signal to the heart signal.

In general, the oscillating electrical signal will be a constant current signal, and this is preferably applied to the thorax of the patient by means of a pair of electrodes applied externally of the thorax. Each electrode of this electrode pair may preferably be provided in an electrode pad assembly, which also includes an appropriate one of the heart or lung sensing electrodes.

The two electrode pairs may be combined into a single four electrode assembly which can then simply be positioned across the front of the chest as a single assembly.

BRIEF DESCRIPTION OF THE DRAWINGS

A number of preferred embodiments of the invention will now be described with reference to the accompanying drawings, in which.

DESCRIPTION OF THE PREFERRED EMBODIMENTS

In accordance with the invention, an oscillating electrical signal is applied to the thoracic cavity to produce an electrical field within which voltage measurements can be made, to thereby determine changes in heart and lung volume. In accordance with the embodiment of the invention illustrated schematically in FIG. 1, the oscillating current signal is a constant current signal at a frequency of approximately 100 KHz. The constant current oscillating signal is applied to the thoracic cavity by means of the constant current electrodes 1 and 2, attached to the chest wall. The electrodes 1 and 2 are connected to a 100 KHz constant current oscillator 3 (FIG. 4), via appropriate resistors R1 and R2. The constant current source 3 supplies a current typically in the range of from 1 to 5 mA, for example 2 mA, at the electrodes 1 and 2.

Figure 1:
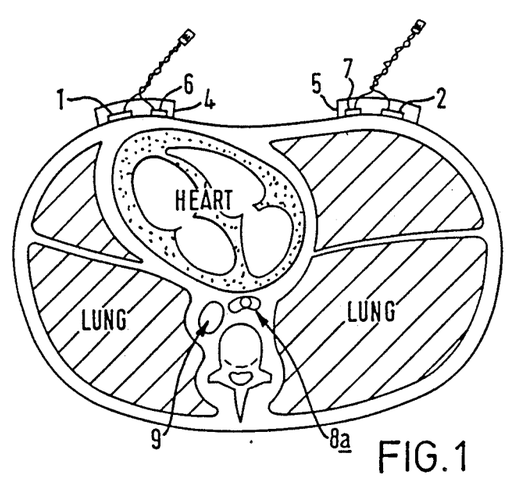
FIG. 1 is a schematic section of the thoracic cavity with electrodes in place.
Figure 2:
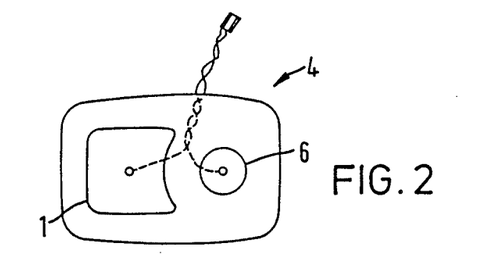
FIGS. 2 and 2a are illustrations of electrode assemblies.

The electrodes 1 and 2 are accommodated in electrode pads 4 and 5, including sensing electrodes 6 and 7 respectively. Two oesophageal electrodes 8a and 8b are also provided on an oesophageal probe 10 which is located in the oesophageal lumen of the patient. The oesophageal probe 10 may be, for example, of the kind described by Baker and McLeod, or of the kind described in European Patent Application No. 81305041.6, or hereinafter. FIG. 1 also shows the position of the aorta 9. The probe 10 is so positioned in the oesophagus that the electrodes 8a and 8b are located in the lower oesophagus, so that 8ais approximately 35 cms from the lips. Each of the electrode pads 4 and 5 has structure as generally indicated in FIG. 2. The electrode pad 4 comprises an adhesive backing material, for example paper, plastics film, or plastics foam which supports and locates the electrodes 1 and 6.

The electrodes 1 and 6 are preferably "gel" electrodes of conventional type consisting of a silver-plated metal electrode with an overlying water-based gel containing dissolved silver chloride as a conductive electrolyte.

The electrode pads 4 and 5 are applied to the chest in approximately symmetrically positions either side of the mid-line, with the left side electrode assembly positioned generally over the apex of the heart. Each electrode is provided with two wires, leading to a connection to a combined wiring loom, for connection to a console unit.

Figure 2A:
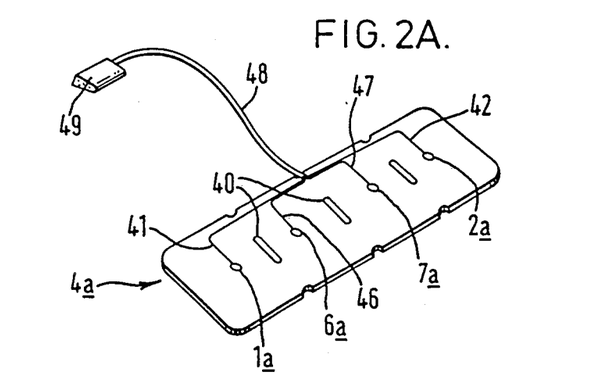
Figure 3:
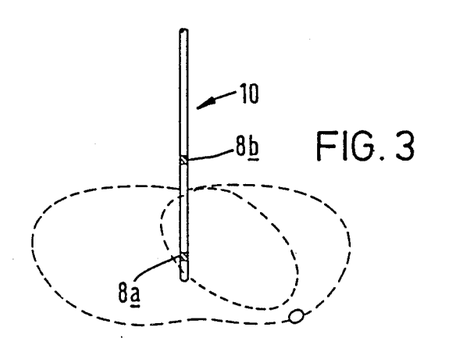
FIG. 3 is a schematic representation of the field of operation of electrodes in accordance with the invention.

An alternative and preferred electrode support structure in the form of a harness is illustrated in FIG. 2a. In FIG. 2a like parts are designated by like reference numerals. The electrode support structure of FIG. 2a comprises a foam rubber support 4a having four electrodes 1a, 6a, 7a and 2a respectively mounted thereon in a manner similar to that illustrated in FIGS. 1 and 2. The electrodes 1a, 6a, 7a and 2a may be of the gel type, as described above. Cut-outs 40 serve to increase the flexibility of support 4a, and also to bleed off any conductive gel which might tend to track across from one electrode to another. Respective conductors 41, 46, 47 and 42 lead from the electrodes to a multi-way non-reversible connector 49, via lead 48. In an alternative embodiment, a snap connector may be provided on support 4a, for electrical connection to electrodes 1a, 6a, 7a and 2a.

The surface of support 4a is covered with a suitable medically acceptable contact adhesive, to retain the support in position on the chest of the patient. A removable backing (not shown) may be provided to protect the adhesive until the support is used.

The generated field potential between the electrode 1 and the electrode 8a or 8b provides a signal which reflects changes primarily in cardiac volume, although the signal will contain some "crosstalk", due to changes in lung volume.

Similarly, the generated field potential between electrode 2 and electrodes 8a or 8b provides a signal which reflects changes in the volume of the right lung. Again, some crosstalk will be present, due to changes in cardiac volume.

Figure 4:
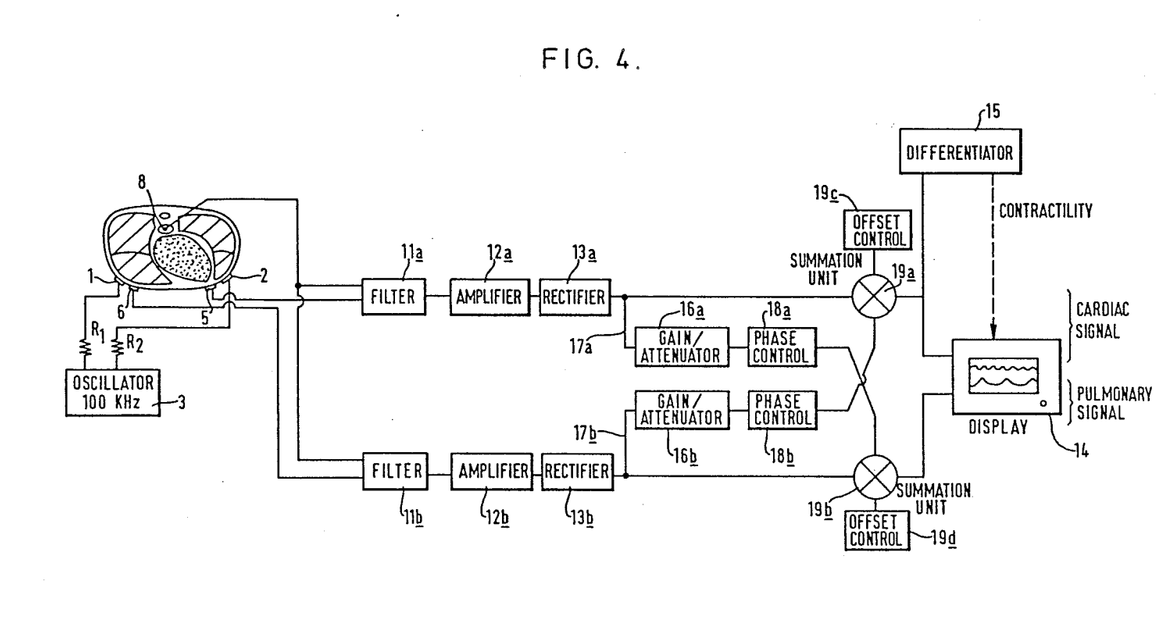
FIG. 4 is a block circuit diagram of apparatus according to the invention.

FIG. 4 also illustrates the circuitry necessary to obtain the desired signal from the electrodes 5 and 6. The cardiac potential developed between electrodes 8 and 5 is applied to a first amplification channel, constituted by filter 11a, amplifier 12a, and rectifier 13a. Filter 11a filters the signal, and passes it to amplifier 12a, from where it is rectified by rectifier 13a. A visual display is provided by display device 14a. Display device 14a may be of any desired kind, for example a chart recorder, cathode ray tube, etc. Similarly, electrodes 6 and 8 provide an input to filter 11b, and corresponding elements 12b and 13b. Crosstalk between the two channels is reduced by arranging for a correcting signal to be added to each respective channel, derived from the other channel, via links 17a and 17b respectively. The signal derived from rectifier 13a is fed via link 17a to a variable attenuator 16a, and a variable phase shifter 18a, and is added to the signal from rectifier 13b by means of summer 19b, with variable offset control 19d. Similarly, a proportion of signal derived from rectifier 13b is fed back through link 17b, variable attenuator 16b, and variable phase control 18b, to summer 19a which variable offset control 19c. The gain controls 16a and 16b may be manual, or automatically operated. Thus, a correcting signal derived from the cardiac signal may be applied to the pulmonary signal, to reduce the cardiac component in the output, and a correcting signal derived from the pulmonary signal may be applied to the cardiac signal. The correcting signal may be adjusted in magnitude, either manually or automatically, and may be provided with means for phase shifting, to minimize the effect of the interference produced by the unwanted signal.

In addition, the cardiac channel may optionally be provided with a differentiator 15, for reasons which will be described in more detail below.

By this means, changes in cardiac or pulmonary impedance may be derived, relatively free of interference arising from the adjacent organ. Means may be provided for optimizing the amplitude and/or phase of the correcting signal, by conventional means, so as to obtain the maximum desired signal.

As can be seen from FIG. 4, the necessary electronics is relatively simply, and consists essentially of a filter, amplifier and rectifier attached to each electrode pair.

The potential generated between the pulmonary electrode 6 and the oesophageal electrodes will typically be of the order of 30 milivolts with a difference between end-inflation and end-expiration of approximately 0.6 to 0.8 milivolts. The potential generated between the cardiac electrode 5 and the oesophageal electrode 8 will generate a voltage of a similar magnitude with a difference from ventricular end-diastolic voltage and ventricular end-systolic voltage of about 0.2 milivolts.

Figure 17A:
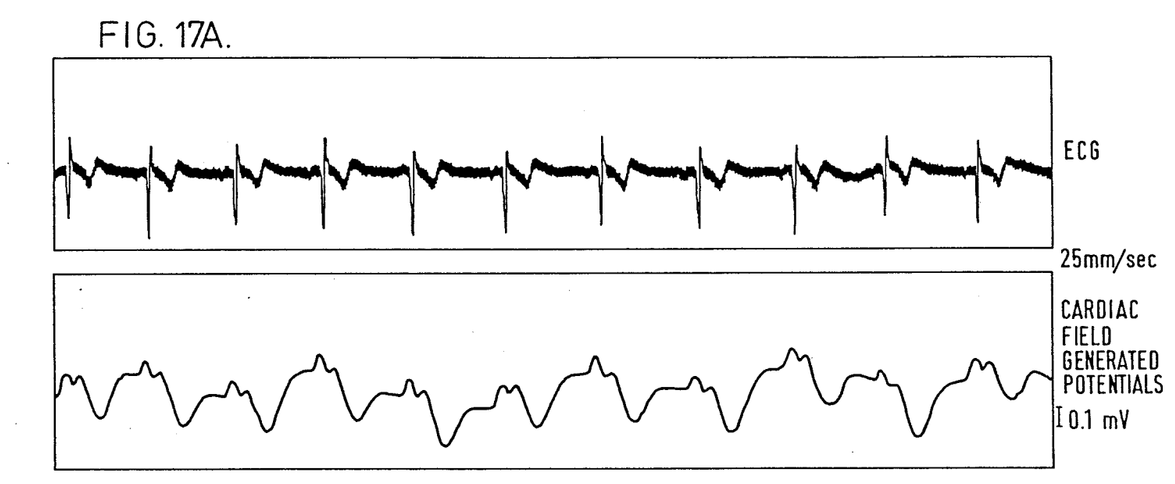
FIGS. 17a and 17b illustrate cardiac and pulmonary traces.

FIG. 17a shows a recording of cardiac field generated potentials e.g. from channel 11a, 12a, 13a in FIG. 4 together with a synchronously recorded ECG (25 mm/sec). There is a small swing in the cardiac field trace, associated with pulmonary ventilation. A trial and ventricular ejection is accompanied by a decrease in voltage (measured downwards).

In this example distinct changes in generated potential can be seen in association with the P wave (contraction of the atria) and a large-scale deflection associated with ventricular contraction. We have found that increased stroke volume is associated with the increase in the voltage change recorded during ventricular ejection; similarly a decrease in stroke volume is associated with a decrease in the amplitude of the signal. Further processing of the signal may yield further useful information. In particular if the signal is differentiated with respect to time, then an index is obtained which can be taken as a measure of the rate of ventricular ejection or cardiac contractility. Changes in cardiac contractility are often found in diseased hearts.

Figure 17B:
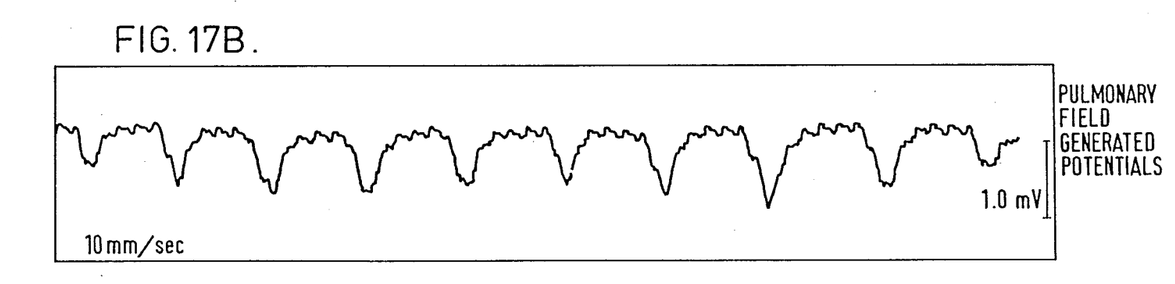

FIG. 15b shows a recording of the pulmonary field generated potentials showing the clear changes between inspiration and expiration, together with the small cardiac signal detected as cross-talk in this channel. A signal is obtained for both cardiac (Vc) and pulmonary (Vp) electrodes. The chosen cardiac output signal is then (Vc−f(Vp) where f is typically less than unity.

The effect of interference in the cardiac signal produced by positive pressure ventilation of the patients lungs can be minimized by making measurements only during periods of apnoea when the ventilator has been switched off for a short period of time. To this end, apparatus in accordance with the invention may be provided with a sensor (e.g. a flow or pressure sensor) placed in the patients breathing circuit for sensing when the ventilator is switched off. The apparatus according to the invention may be arranged to record data during apnoea and indicate to a clinician that an adequate sample has been obtained so that ventilation may be restarted.

As discussed above, the signals observed or utilized by the clinician may be analogue signals, for example the field generated potentials themselves. In alternative embodiments, however, the measured potentials may be subjected to further electronic processing either by analogue means or by computerized means following digitisation. For example, changes in the generated voltage may be measured only during certain phases of the cardiac cycle. This would be performed, for example, by triggering the measurement sequence from the ECG signal and measuring during the ventricular ejection period only. A number of measurements sampled over several cycles may provide a useful average value for that patient.

Although the foregoing description refers to an oesophageal electrode positioned on a catheter introduced into the oesophagus via the mouth, the catheter could also be positioned in the oesophagus via the nasal route, particularly, for example, for long-term use in conscious patients, oesophageal electrodes may be incorporated into a probe dedicated to that one function or into, for example a catheter which also services other functions such as gastric drainage.

Alternatively, the oesophageal probe may take the form of a small conductive "pill" attached to a fine insulated wire. The pill then constitutes the electrode, and may be swallowed by the patient and located in the lower oesophagus by taping the connecting wire to the side of the mouth. This may enable measurements to be made more conveniently in patients who are ambulatory. Utilizing a probe of this kind, apparatus in accordance with the invention may be constructed which is portable, and may be carried on the body of an ambulatory patient.

Figures 5, 6, 7, 8, 9:
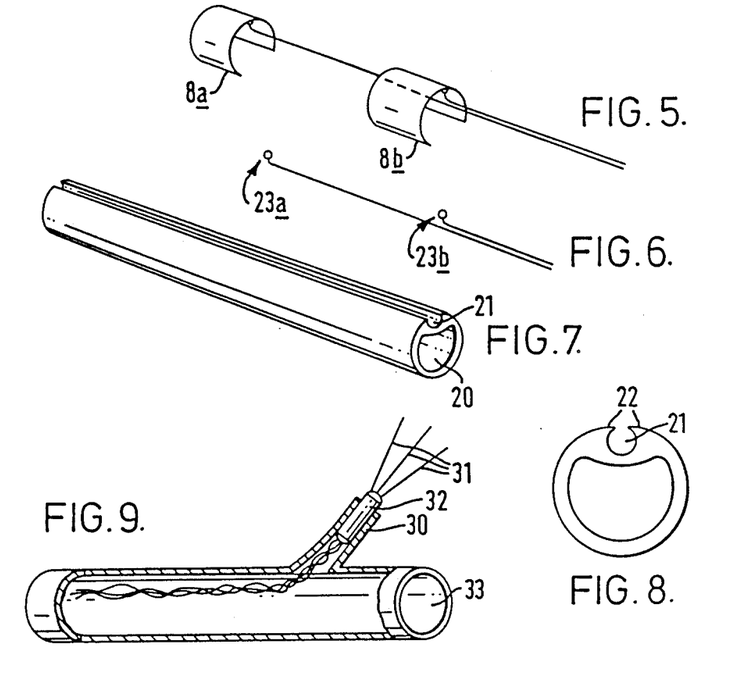
FIGS. 5 to 9 illustrate the construction of oesophageal probes.

The electrodes provided on the oesophageal probe may be coupled to wiring which is contained within the lumen of the probe, and which penetrates the wall of the probe before being affixed or incorporated into the electrodes. Thus, in a probe of the kind disclosed in European Patent Specification No. 81305041.6, wires may be passed through one of the internal lumens of the oesophageal probe, and brought out through the wall of the probe only in the region of the respective electrode. When wires enter and leave the lumen of such a probe it is necessary to ensure that the point of entry and exit is airtight. This is conveniently done by applying a quantity of adhesive or plastic solution the annular space created.

Where several wires have to enter or leave the probe a side-arm 30 can be provided, as shown in FIG. 9. FIG. 9 shows the upper or proximal end of an oesophageal probe, the distal end of which may be for example, as shown in European Patent Specification No. 81305041.6, fitted with suitable electrodes. A wiring loom 31 is connected to the various electrodes and brought out through side-arm 30. A removable airtight plug 32 formed from a suitable sleeve and adhesive is secured in the side-arm. By this means several wires can enter or leave the probe lumen 33 without allowing any pressurized gas contained in the lumen to escape.

Alternatively and preferably, a groove may be provided in an oesophageal probe, as illustrated in FIGS. 7 and 8. The groove may be of the form illustrated, i.e. relatively open, or alternatively it may be roofed over, having been formed by extrusion, and then subsequently slit along all or part of its length by a sharp blade so that the groove is overhung on either side by two lips of plastic. FIGS. 7 and 8 illustrate a perspective and end view respectively of a section suitable for use in making an oesophageal probe. The probe includes at least one closed lumen 20, and a channel 21 which is almost closed by beads 22. A wiring loom as illustrated in FIG. 6 may be laid in the channel 21, so as to obviate the need for perforating the lumen 20. Electrodes 8a and 8b may be affixed to contacts 23a, 23b respectively, on the exterior of the oesophageal probe. The electrodes 8a and 8b take the form of semi rigid conductive members, forming an incomplete circle around the probe 10. Typically, the electrodes will extend over about ⅔ of the circumference of the probe. The electrodes 8a and 8b may be secured to the exterior wall of the probe 10 by means of an adhesive. An electrically conductive adhesive applied to the electrode/probe interface is preferred since this does not interfere with the electrical continuity. Alternatively, the electrodes may be positioned on the probe body by crimping.

The wiring loom may be secured in the groove 21 by means of an adhesive or a sealant.

The technique may be applied with relative ease to metallic electrodes, but the electrodes 8a and 8b could equally well be composed of conductive rubber or plastics material. In this case, the electrodes may encircle the probe body completely. The adhesive or crimping processes may be used with these materials, as with metallic electrodes.

A suitable electrode applied to the surface of the probe can be conveniently and simply formed by the application of a conductive (metal loaded) adhesive (e.g. epoxy based or a cyano-acrylate type adhesive) to the surface of the probe. The film may be applied by means of a suitable blade, roller or brush. During the application of the film the connecting wires can be incorporated into the adhesive film. The electrode can then be allowed to cure and harden.

Figure 13:
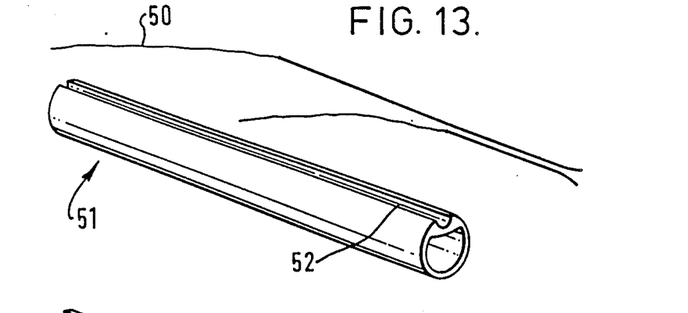
FIGS. 13 to 16 illustrate alternative oesophageal probes.
Figure 14:
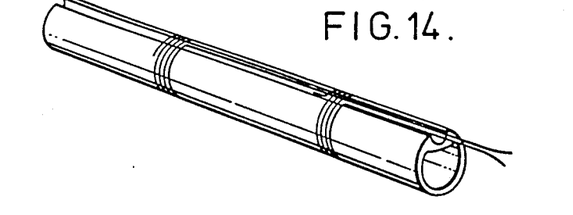

In an alternative embodiment, electrodes may be formed as illustrated in FIGS. 13 and 14, from a length of conductive material 50 (e.g. precious metal or conductive plastic) which is wrapped around the body of the probe in a spiral fashion typically for about 5 turns. The distal end of the coil electrode formed can be cemented in place or buried into the surface of the probe. The proximal end can be connected to wire which runs either on the surface of the probe or in a groove as described above. In practice, several wire electrodes may be formed together as a loom and affixed to the probe. Each electrode may then finally be forced by wrapping the electrode around the probe. By this means, a flexible electrode with a large surface area can be easily created.

Figure 15:
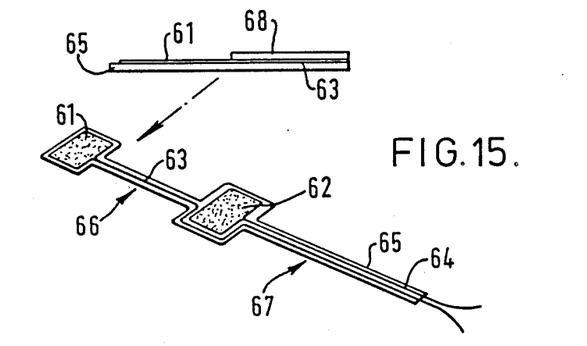
Figure 16:
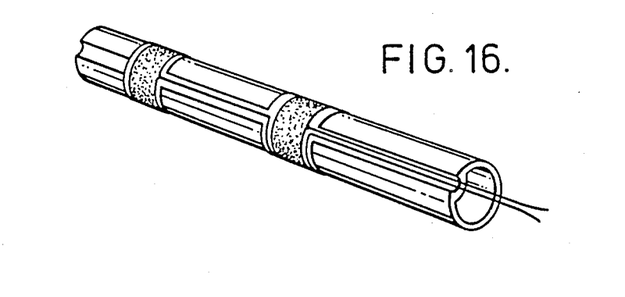

In a further alternative embodiment illustrated in FIGS. 15 and 16, an electrode and its connecting wires are formed in the manner of a thin printed circuit in which the electrodes 61, 62 and their connecting wires 63, 64 respectively are formed on a flexible circuit backing material 65 manufactured by one of the conventional printed-circuit techniques e.g. photo-etching or printing. Such circuitry can be applied to various bases, for example PVC which can be bonded to the surface of the probe. The electrode assembly may thus be added to the probe in a relatively simple manner. The electrodes are formed by enlarged regions of the printed circuit material, and may be fixed by adhesive to the body of the probe in the appropriate positions.

The provision of the two electrodes 8a and 8b in conjunction with cardiac electrode 1 can provide particular benefits in the measurement of ECG. The traditional way of measuring ECG is by means of a number of surface electrodes applied to the chest. ECG signals measured using an oesophageal electrode as disclosed above shows signals arising in the atria (the P wave complex) very clearly, because the oesophagus lies adjacent to the atria. The shape of the P wave complex may also differ from that conventionally seen, since the electrical axis of the atria during atrial contraction is being observed from a non-standard position.

The same consideration also applies to the QRS complex which is the result of ventricular contraction.

Figure 10:
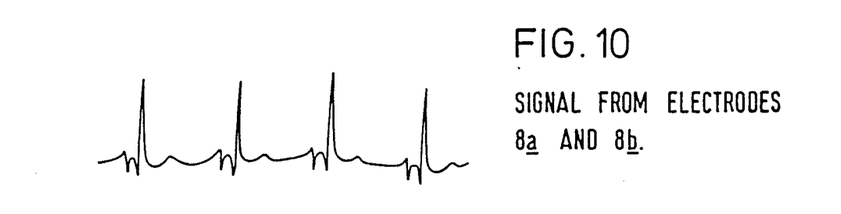
FIGS. 10 to 12 illustrate various ECG traces.
Figure 11:
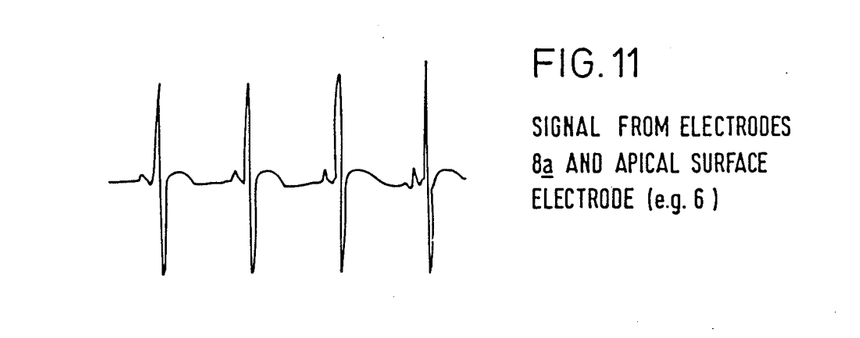
Figure 12:
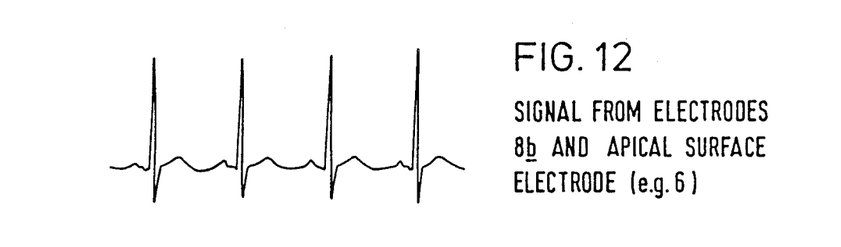

If the two oesophageal electrodes are used in combination with a surface electrode placed, for example, near the apex of the heart, then two ECG signals can be obtained, the first utilizing the two oesophageal electrodes 8a and 8b, the second utilizing electrode 6, in combination with electrode 8a and the third utilizing electrode 6 in combination with electrode 8b. Examples of traces obtained from such signals are illustrated in FIGS. 10, 11 and 12 respectively. The first ECG signal, which is shown in FIG. 10, gives a particularly clear view of the atrial components of the ECG, whilst the second and third (FIGS. 11 and 12) give a particularly clear view of the ventricular complex, and as such may be particularly useful in examining changes in the ST segment of the QRST system which may provide a sensitive monitor of hypoxic or ischaemic changes in the ventricles.

Thus, by the provision of a plurality of electrodes in the oesophagus, and electrodes on the surface of the body, together with a switching systems and appropriate amplifiers, it is possible for the physician to observe and display an oesophageal ECG, or an oesophageal-/apical ECG, depending upon whether he wishes to observe details of atrial or ventricular activities. Accordingly, apparatus according to the invention may incorporate means for measuring ECG activity between one or more pairs of electrodes. Such means may preferably include means for filtering signals obtained from the electrodes so as to remove therefrom the high frequency signals used in to generate field potentials (100 kHz), allowing the local frequency signals (1–100 Hz) to remain.

It should of course be understood that the invention is not limited to the specific embodiment disclosed above, and a wide range of other specific arrangements are envisaged within the scope of the appended claims.

I claim:

1. A method of measuring cardiac activity, which method comprises generating an oscillating electrical signal, applying the oscillating electrical signal to the the thorax of a patient, providing in the oesophagus of the patient an oesophageal probe including a first electrode, providing a second electrode on the left side of the chest of the patient in a position such that measurement of voltage between the said first and second electrodes provides a measure of cardiac volume, and measuring the voltage induced between the first and second electrodes and producing therefrom an output signal indicative of cardiac activity in the patient.

2. A method as claimed in claim 1, wherein a third electrode is employed, the third electrode being positioned on the chest of the patient at a position on the right side of the chest generally corresponding with that of the second electrode of the left side of the chest, whereby measurement of voltage between the said first and third electrodes provides a measure of volume of the right lung of the patient, and wherein a second output is produced, dependant upon the electrode signal induced between the first and third electrodes, the said second output being indicative of pulmonary activity.

3. A method as claimed in claim 2, and including the step of varying one of the said output signals, in dependence upon the value of the other of the said output signals.

4. A method as claimed in claim 3, including the step of adding to the said one of the said output signals, a correcting signal consisting of a proportion of the other of the said signals.

5. A method as claimed in claim 4, including the step of varying the amplitude of the said correcting signal.

6. A method as claimed in claim 4 including varying the phase of the correcting signal with respect to the said first output signal.

7. A method as claimed in claim 1, wherein the oscillating electrical signal applied to the thorax of the patient is a constant current signal.

8. A method as claimed in claim 1, wherein the second and third electrodes are maintained in a desired position on the chest of the patient by means of a harness.

9. A method as claimed in claim 8, wherein each one of chest the said pair of electrodes is provided in the form of a respective electrode pad, which pad also includes a respective one of the said second and third electrodes.

10. Apparatus for measuring cardiac and/or pulmonary activity, which apparatus comprises
   means for generating an oscillating electrical signal,
   means for applying the oscillating electrical signal to the thorax of a patient,
   an oesophageal probe including a first electrode,
   a second electrode adapted to be positioned on the left side of the chest of the patient over the heart, whereby measurement of voltage between the said first and second electrodes provides a measure of cardiac volumes,
   a third electrode adapted to be positioned on the chest of the patient at a position on the right side of the chest generally corresponding with that of the second electrode of the left side of the chest, whereby measurement of voltage between the said first and third electrodes provides a measure of volume of the right lung of the patient,
   means for measuring the voltage induced between the first and second, and the first and third electrodes respectively, and for thereby providing first and second output signals respectively, indicative of cardiac and pulmonary activity respectively.

11. Apparatus as claimed in claim 10, including means for varying one of the said output signals, in dependence upon the value of the other of the said output signals.

12. Apparatus as claimed in claim 11, wherein the means for varying the said one of the output signals includes means for adding to the said one of the said output signals, a correcting signal consisting of a proportion of the other of the said signals.

13. Apparatus as claimed in claim 12, including means for varying the amplitude of the said correcting signal.

14. Apparatus as claimed in claim 12, including means for varying the phase of the correcting signal with respect to the said first output signal.

15. Apparatus as claimed in claim 11, wherein the oscillating electrical signal applied to the thorax of the patient is a constant current signal.

16. Apparatus as claimed in claim 11, including a harness for maintaining the said second and third electrodes in a desired position on the chest of the patient.

17. Apparatus as claimed in claim 11, wherein the means for applying the oscillating electrical signal to the thorax of the patient includes a pair of electrodes adapted to be affixed to the chest of the patient.

* * * * *